United States Patent [19]

Holben

[11] 4,350,285

[45] Sep. 21, 1982

[54] VISCOSITY REGULATING APPARATUS AND METHOD

[75] Inventor: Eugene F. Holben, Haddonfield, N.J.

[73] Assignee: Conometer Corporation, Gibbsboro, N.J.

[21] Appl. No.: 226,742

[22] Filed: Jan. 21, 1981

[51] Int. Cl.³ .............................................. G05D 24/00
[52] U.S. Cl. ................................... 236/1 R; 137/13; 137/92; 73/56
[58] Field of Search ........................ 137/4, 13, 92, 565; 73/54, 55, 56, 58; 236/1 R

[56] References Cited

U.S. PATENT DOCUMENTS

| | | | |
|---|---|---|---|
| 2,771,770 | 11/1956 | Bowman | 73/55 |
| 3,138,950 | 6/1964 | Welty | 73/56 X |
| 3,277,916 | 10/1966 | Deming | 137/92 X |
| 3,938,369 | 2/1976 | de Bok | 73/55 |

Primary Examiner—Alan Cohan
Attorney, Agent, or Firm—Weiser, Stapler & Spivak

[57] ABSTRACT

Apparatus and method for measuring the viscosity of a fluid by drawing a sample of the fluid through a first flow restrictor (24) and forcing the sample through a second flow restrictor (28) having flow restriction characteristics which are identical to the flow restriction characteristics of the first flow restrictor. The difference in pressures of the sample at the exit of the first flow restrictor and at the entrance to the second flow restrictor provides a measure of the viscosity of the fluid and may be used to vary the temperature of the fluid to control its viscosity.

17 Claims, 4 Drawing Figures

VISCOSITY REGULATING APPARATUS AND METHOD

TECHNICAL FIELD

The present invention relates, in general, to fluid control and, in particular, to an apparatus and method for regulating the viscosity of a fluid.

BACKGROUND ART

The economical operation of any power plant or diesel engine is dependent upon efficient energy conversion. Peak efficiency is achieved when fuel combustion efficiency is greatest resulting in maximum utilization of the energy of the fuel. At the same time, complete combustion prevents carboning of the heat exchanger walls in steam boilers or cylinder and valve chambers of diesel engines, thus reducing maintenance coats. For a given fuel burner design, the combustion efficiency is affected by the viscosity of the fuel and, therefore, it is important that the fuel viscosity be controlled accurately.

In addition, efficient operation of the pump which supplies the fuel to the power plant or diesel engine is dependent upon the viscosity of the fuel. If the viscosity is too high, the delivery pressure of the pump may become much too great and an excessive amount of energy will be required to operate the pump.

One way to maintain relatively constant viscosity is to use a 2 diesel fuel which has characteristics at ambient temperature conditions which are ideal for efficient use. However, such fuel is very expensive.

A very common practice today is to use a cheaper grade of fuel and to control its viscosity by heating the fuel in accordance with in-line measurements of different characteristics of the fuel. One such practice involves measuring the fuel temperature as it leaves a steam heated heat exchanger and varying the amount of steam being passed through the heat exchanger to vary the fuel temperature and thereby control the fuel viscosity. Such an approach, however, is inadequate in that for a given grade of fuel, a particular temperature may result in a range of viscosities because of variations in the production of the fuel.

Thus, a preferred approach is to measure the fuel viscosity directly with a viscometer which is inserted in the fuel line and to automatically control the heater according to the viscosity measurements. U.S. Pat. No. 2,771,770 shows a viscometer having a pump which forces a portion of the fuel passing through a fuel line through a capillary tube. The pressure drop from the inlet of the tube to the outlet of the tube is a direct measure of the viscosity of the fuel passing through the tube. A drawback of this arrangement is that line pressure surges, for example, caused as each engine injector is fired, vary drastically the pressure measurements across the capillary tube. The outlet end of the tube is exposed to such surges and, therefore, "sees" these surges, while the inlet end of the tube is isolated from these surges by the pump and the capillary tube.

U.S. Pat. No. 3,938,369 shows a viscometer similar to the one shown in U.S. Pat. No. 2,771,770, except that a second capillary tube is added in series with the first one in the later issued patent. The second tube serves to dampen pulsations at the outlet of the viscometer, whereby the first capillary tube, which is the measuring tube, is isolated from such pulsations at its inlet and outlet by the pump and the dampening capillary, respectively. Although the arrangement in U.S. Pat. No. 3,938,369 reduces the effect of line surges on the viscosity measurements, it fails to provide a complete solution to the problem. To the extent that the flow restriction through the pump is different from the flow restriction of the damping capillary tube, either when the viscometer is put into service or with wear on the pump, the inlet and outlet of the measuring capillary tube will be isolated from pulsations to different extents causing incorrect viscosity measurements.

DISCLOSURE OF THE INVENTION

Accordingly, one objective of the present invention is to provide a new and improved viscometer.

Another objective of the present invention is to provide new and improved apparatus especially useful for properly regulating the viscosity of fuel being supplied to an engine.

A further objective of the present invention is to provide apparatus which overcomes the shortcomings and limitations of the prior art.

Yet another objective of the present invention is to provide apparatus which is relatively simple in construction and inexpensive to fabricate.

Apparatus constructed in accordance with the present invention includes a viscometer housing connected into a fluid line between two points for flowing fluid from the fluid line through the housing and returning the fluid flowing through the housing to the fluid line. Also included are identical first and second flow restrictors and a pump connected between the first and second flow restrictors. The pump diverts a portion of the fluid flowing through the housing through the first flow restrictor, the pump itself and the second flow restrictor. The apparatus further includes means for sensing the pressure of the fluid entering and leaving the pump. The difference in the two pressures is a measure of the viscosity of the fluid flowing through the fluid line and is used to control means which vary the viscosity of the fluid flowing through the fluid line as a function of the pressure difference.

BRIEF DESCRIPTION OF THE DRAWINGS

Referring to the drawings.

BEST MODE OF CARRY OUT THE INVENTION

Figure 1:
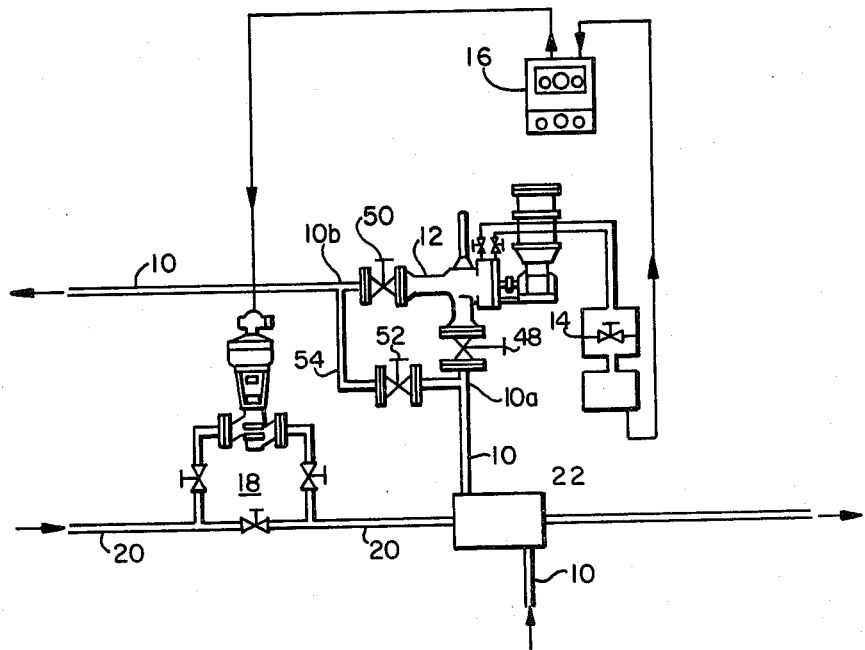
FIG. 1 is a diagram showing the overall apparatus incorporating the present invention.

Referring to FIG. 1, apparatus for regulating the viscosity of a fluid flowing through a fluid line, constructed in accordance with the present invention, includes a fluid line 10 and a housing 12 connected between points 10a and 10b of the fluid line. Fluid line 10 may serve to carry fuel oil from a storage tank (not shown) to a diesel engine (not shown). For the embodiment of the invention being described, housing 12 serves to contain and support various viscometer components for regulating the viscosity of the fuel passing through fuel line 10. The details of housing 12 and the other viscometer components will be considered in greater detail below. At this point, it will be sufficient to understand that the viscometer receives fuel flowing through fuel line 10 and, in conjunction with a differential pressure transmitter 14 and a controller 16, develops a control signal representative of the viscosity of the fuel. In particular, a pneumatic signal which is proportional to the differential pressure measured by the viscometer is transmitted by differential pressure transmitter 14 to controller 16. The controller compares the signal from the differential pressure transmitter to a signal representative of the desired viscosity and if the measured viscosity is not the same as the desired viscosity, the control signal developed by the controller provides a measure of the difference. The control signal, in turn, controls a steam control valve unit 18 which regulates the amount of steam passing through a pipe 20 to a heater 22 through which fuel line 10 extends. In this way, the temperature of the fuel is varied, at a point upstream of the viscometer, as a function of the viscosity of the fuel measured by the viscometer. Differential pressure transmitter 14, controller 16, steam control valve unit 18 and heater 22 may be standard, commercially available units.

Figure 2:
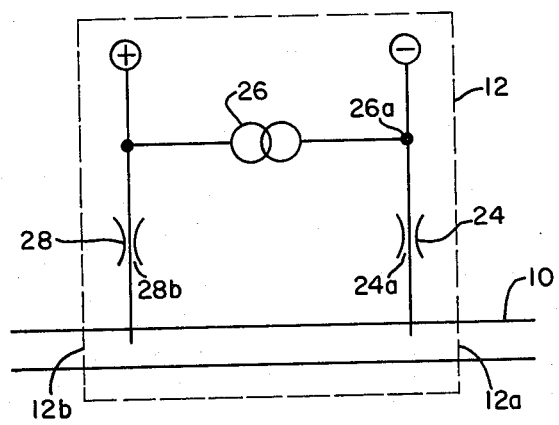
FIG. 2 is a schematic diagram of the present invention.

FIG. 2 schematically illustrates the manner in which a viscometer, constructed in accordance with the present invention, functions. Fuel from fuel line 10 flows into housing 12 through an inlet 12a and leaves the housing through an outlet 12b. A portion of the fuel passing through housing 12 passes through a restricted flow path which includes a first flow restrictor 24, a pump 26 and a second flow restrictor 28. In particular, pump 26 draws a portion of the fluid introduced into housing 12 through flow restrictor 24 and forces this drawn portion of fluid through the restrictor 28. By selecting flow restrictors having identical flow restriction characteristics, the pressure drop across each is identical and inlet 26a and outlet 26b of pump 26 are equally isolated from line surges which may appear at inlet 24a to flow restrictor 24 and outlet 28b from flow restrictor 28. The differential pressure across pump 26, equal to the sum of the pressure drops across the two flow restrictors and equal to twice the pressure drop across either flow restrictor when the flow restrictors have identical flow restriction characteristics, provides a measure of the viscosity of the fuel flowing through the housing. The differential pressure across pump 26 in available at the terminals identified by the plus and minus signs.

Figure 3:
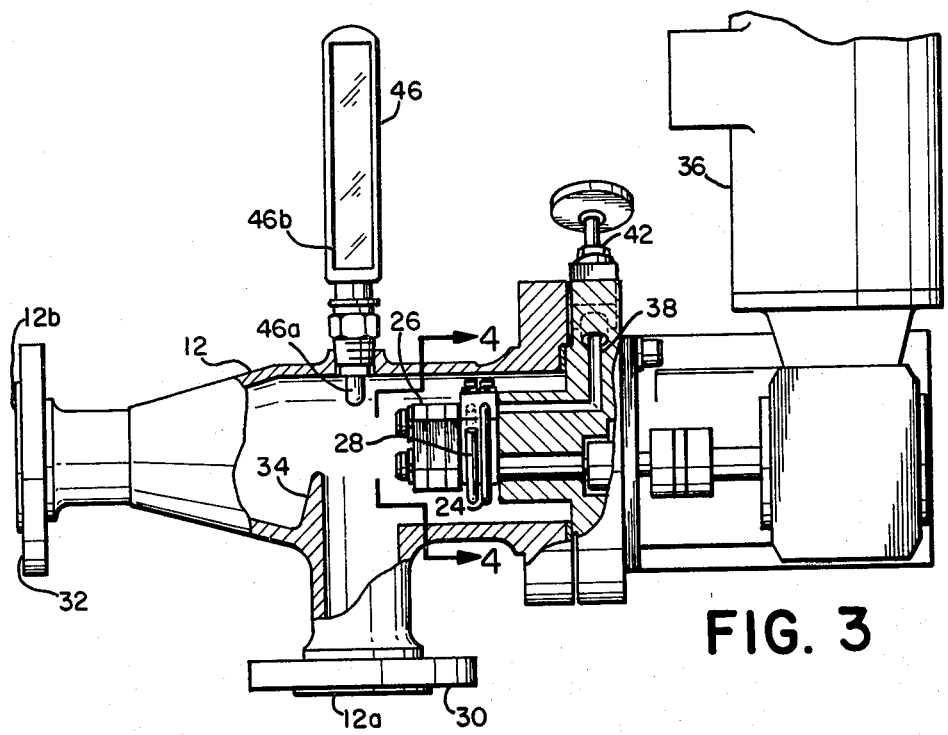
FIG. 3 is a side view, partially broken away, of a viscometer constructed in accordance with the present invention.
Figure 4:
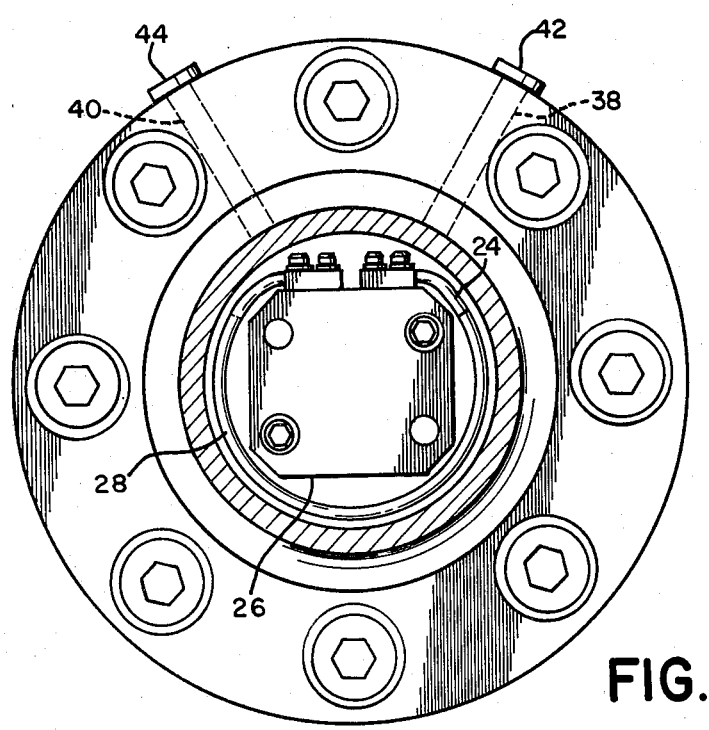
FIG. 4 is a vertical section taken along line 4—4 of FIG. 3.

Referring to FIGS. 3 and 4, a viscometer, constructed in accordance with the present invention, includes housing 12 having inlet 12a and outlet 12b adapted to be connected to a fluid line. For the embodiment illustrated in FIGS. 3 inlet 12a is formed by a flange 30 and outlet 12b is formed by a flange 32. The main flow path of the fuel through housing 12 is from inlet 12a, around a web 34, to outlet 12b.

The viscometer of FIGS. 3 and 4 also includes first and second flow restrictors 24 and 28 and pump 26. Flow restrictors 24 and 28, disposed within housing 12, are in the form of curved capillary tubes which are carried by and extend around pump 26 also disposed within the housing. The pump may be a standard gear pump which draws fluid into capillary tube 24 through the inlet of capillary tube 24 and forces the drawn fluid through capillary tube 28 and out through the outlet of capillary tube 28. Pump 26 is coupled to a motor 36, mounted on housing 12, which imparts a constant speed drive to the pump which, in turn, maintains a constant flow through capillary tubes 24 and 28.

Two fluid paths 38 and 40 extend from the entrance and exit, respectively, of the pump to the surface of the housing and terminate in threaded fittings 42 and 44, respectively. These fittings are the minus and plus outputs of the viscometer and are adapted to receive valve and hose nipple units which, in turn, are connected through hoses to a differential pressure transmitter for sensing the pressure of the fluid entering and leaving pump 26.

The inlet of capillary tube 24 and the outlet of capillary tube 28 are removed from the main flow path of the fuel through housing 12 from housing inlet 12a to housing outlet 12b. Such an arrangement enhances the accuracy of the viscosity measurements in that the inlet of capillary tube 24 and the outlet of capillary tube 28 are in a generally quiescent region so that the points at which the differential pressure measurements are derived, namely the inlet and outlet of the pump, are less subject to abrupt changes in the fuel flow in line 10. However, in order to provide some degree of controlled circulation of the fluid being measured, web 34 is arranged to block direct through passage of the fluid and instead causes some fluid flow toward the inlet of capillary tube 24 and the outlet of capillary tube 28.

A viscometer shown in FIG. 3 also includes a thermometer 46 mounted on housing 12 having its temperature sensing bulb 46a disposed within the fluid flowing through the housing and its temperature indicating scale 46b located outside the housing. Although the apparatus of the present invention controls viscosity by the direct development of viscosity measurements, the provision of direct temperature measurements with a thermometer is a desirable feature of such apparatus.

Returning to FIG. 1, the apparatus also may include three valves 48, 50 and 52 which serve to control fluid flow through housing 12 or through a by-pass line 54 or through both. By-pass line 54 is provided to permit uninterrupted flow of fuel through fuel line 10 when the viscometer must be removed for service. In such a case, valves 48 and 50 are closed and valve 52 in by-pass line 54 is opened. Otherwise, valve 52 is closed and valves 48 and 50 are open and the entire flow of fuel in line 10 passes through housing 12. This assumes that housing 12 has a capacity capable of passing the full flow of fluid passing through line 10. If not, the three valves 48, 50 and 52 are opened and the cross-sectional areas of by-pass line 54 and the lines carrying valves 48 and 50 are selected to split the flow in fuel line 10 between housing 12 and by-pass line 54 in the desired ratio.

While in the foregoing there has been described a preferred embodiment of the present invention, it should be understood to those skilled in the art that various modifications and changes can be made without departing from the true spirit and scope of the invention as recited in the claims.

I claim:

1. Apparatus for regulating the viscosity of a fluid flowing through a fluid line comprising:
   a fluid line;
   housing means connected between two points in said fluid line for flowing fluid from said fluid line through said housing means and for returning fluid flowing through said housing means to said fluid line;
   first and second flow restrictors having identical flow restriction characteristics;

pump means connected between said first flow restrictor and said second flow restrictor for diverting a portion of fluid flowing through said housing means through said first flow restrictor, said pump means and said second flow restrictor;

means for sensing the pressures of fluid entering and leaving said pump means;

and control means responsive to said sensing means for varying the viscosity of fluid flowing through said fluid line as a function of the difference in said pressures of fluid entering and leaving said pump means.

2. Apparatus according to claim 1 wherein said control means vary the temperature of fluid flowing through said fluid line at a point upstream of said housing means.

3. Apparatus according to claim 2 wherein a section of said fluid line bypasses said housing between said two points.

4. Apparatus according to claim 3 further including means for varying fluid flow through said housing means and said section of said fluid line.

5. Apparatus according to claim 1 wherein said first and second flow restrictors and said pump means are disposed within said housing means.

6. A viscometer comprising:

housing means adapted to be connected between two points in a fluid line for flowing fluid from said fluid line through said housing means and for returning fluid flowing through said housing means to said fluid line;

first and second flow restrictors having identical flow restriction characteristics, said first flow restrictor having an inlet and said second flow restrictor having an outlet which are disposed within said housing;

pump means connected between said first flow restrictor and said second flow restrictor for drawing a portion of fluid flowing through said housing means through said first flow restrictor and for forcing said drawn portion of fluid through said second flow restrictor back into said flow through said housing means;

and means for sensing the pressures of fluid entering and leaving said pump means.

7. A viscometer according to claim 6 further including:

a motor mounted on said housing means;

and means for coupling said motor to said pump means.

8. A viscometer according to claim 6 further including a thermometer mounted on said housing means with its temperature sensing portion disposed within said housing means and its temperature indicating portion located outside said housing means.

9. A viscometer according to claim 6 wherein said first flow restrictor and second second flow restrictor are capillary tubes.

10. A viscometer according to claim 6 wherein said inlet to said first flow restrictor and said outlet from said second flow restrictor are removed from the main flow path of fluid flowing through said housing means.

11. A viscometer according to claim 10 wherein said flow restrictors and said pump means are disposed within said housing means.

12. A viscometer comprising:

a housing having an inlet and an outlet adapted for connection to two points in a fluid line for passing fluid flowing through said fluid line from said housing inlet to said housing outlet;

means within said housing for passing a portion of fluid passing through said housing through a restricted flow path, said means including first and second flow restrictors having identical flow restriction characteristics and a pump connected between said first flow restrictor and said second flow restrictor;

and means for sensing the pressures of fluid passing through said restricted flow path at the entrance and exit of said pump.

13. A viscometer according to claim 12 wherein said first flow restrictor, said second flow restrictor and said pump are removed from the flow path between said housing inlet and said housing outlet.

14. A method for measuring the viscosity of a fluid comprising:

drawing a sample of said fluid through a first flow restrictor and forcing said sample through a second flow restrictor having flow restriction characteristics identical to the flow restriction characteristics of said first flow restrictor;

and measuring the pressures of said fluid sample at the exit of said first flow restrictor and at the entrance to said second flow restrictor.

15. A method for regulating the viscosity of a fluid flowing through a line comprising:

drawing a sample of said fluid through a first flow restrictor and forcing said sample through a second flow restrictor having flow restriction characteristics identical to the flow restriction characteristics of said first flow restrictor;

measuring the pressures of said fluid sample at the exit of said first flow restrictor and at the entrance to said second flow restrictor;

and controlling the viscosity of said fluid flowing through said line in accordance with the difference in said pressures of said fluid sample at the exit of said first flow restrictor and at the entrance to said second flow restrictor.

16. The method according to claim 15 wherein said viscosity of said fluid flowing through said line is controlled by varying the temperature of said fluid.

17. A method according to claim 15 wherein said sample is drawn from a portion of said fluid flowing through said line.

\* \* \* \* \*